US011751998B2

(12) United States Patent
Bohl

(10) Patent No.: US 11,751,998 B2
(45) Date of Patent: *Sep. 12, 2023

(54) SYSTEMS AND METHODS FOR FIXATING, FUSING AND/OR REALIGNING THE SACROILIAC JOINT

(71) Applicant: Dignity Health, San Francisco, CA (US)

(72) Inventor: Michael A. Bohl, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 72 days.

This patent is subject to a terminal disclaimer.

(21) Appl. No.: 17/568,352

(22) Filed: Jan. 4, 2022

(65) Prior Publication Data

US 2022/0117744 A1    Apr. 21, 2022

Related U.S. Application Data

(62) Division of application No. 17/290,094, filed as application No. PCT/US2019/059270 on Oct. 31, 2019, now Pat. No. 11,318,020.

(60) Provisional application No. 62/753,575, filed on Oct. 31, 2018.

(51) Int. Cl.
    *A61F 2/30*    (2006.01)
    *A61F 2/28*    (2006.01)

(52) U.S. Cl.
    CPC .. *A61F 2/30988* (2013.01); *A61F 2002/2835* (2013.01); *A61F 2002/30405* (2013.01); *A61F 2002/30518* (2013.01); *A61F 2002/30622* (2013.01); *A61F 2002/30904* (2013.01); *A61F 2002/30995* (2013.01)

(58) Field of Classification Search
    CPC ............. A61B 17/7055; A61F 2/30988; A61F 2002/30995; A61F 2002/30405; A61F 2002/30518
    See application file for complete search history.

(56) References Cited

U.S. PATENT DOCUMENTS

| 6,364,883 B1 | 4/2002 | Santilli |
| 2006/0106382 A1 | 5/2006 | Gournay et al. |
| 2011/0087292 A1 | 4/2011 | Sandhu et al. |
| 2016/0338714 A1 | 11/2016 | Schoenefeld et al. |
| 2017/0135733 A1 | 5/2017 | Donner et al. |
| 2017/0246000 A1 | 8/2017 | Pavlov et al. |
| 2018/0177535 A1 | 6/2018 | Boulot |

FOREIGN PATENT DOCUMENTS

WO    2006127727 A2    11/2006

OTHER PUBLICATIONS

Patent Cooperation Treaty, International Search Report and Written Opinion, International Application No. PCT/US2019/059270, dated Jan. 13, 2020, 10 pages.

*Primary Examiner* — Javier G Blanco
(74) *Attorney, Agent, or Firm* — Polsinelli PC

(57) ABSTRACT

Various embodiments of a coupler and an intradiscal implant for alignment and fusion of the sacroiliac joint are described herein.

11 Claims, 20 Drawing Sheets

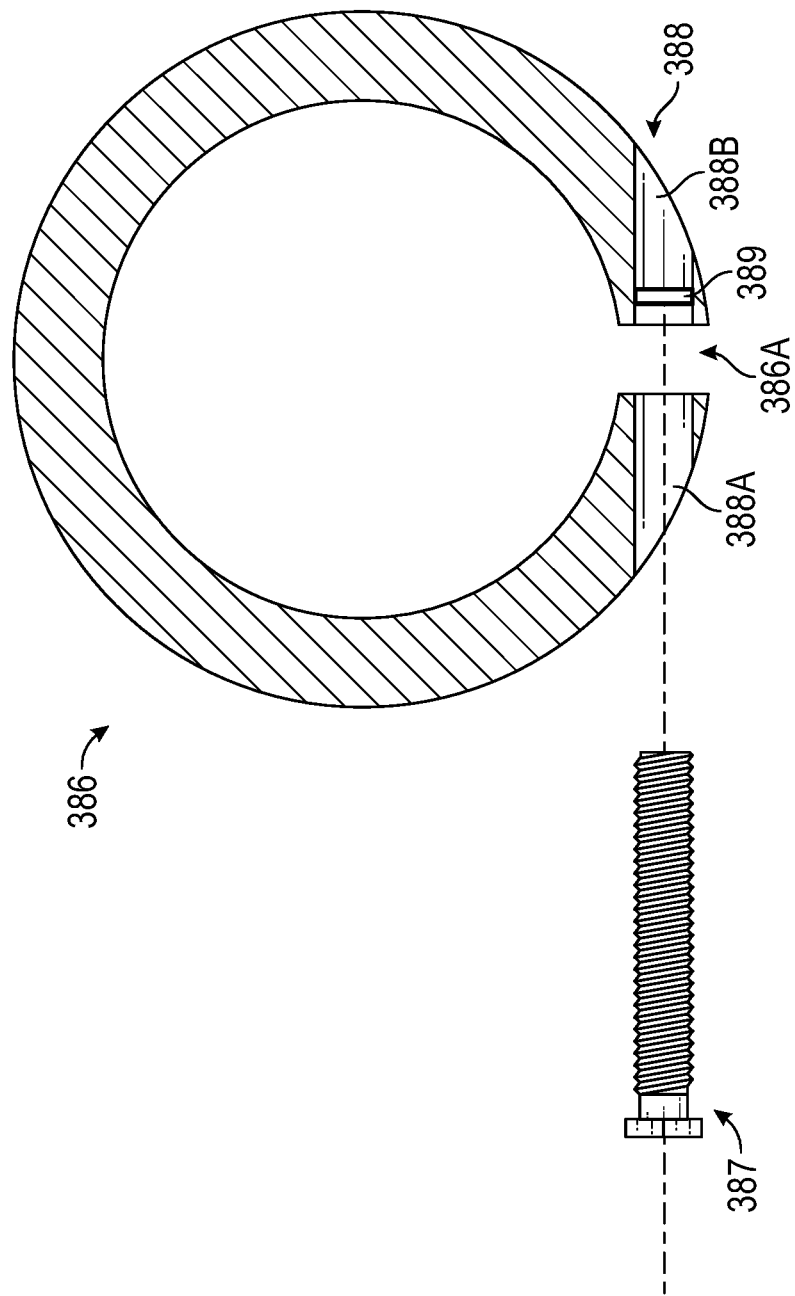

SYSTEMS AND METHODS FOR FIXATING, FUSING AND/OR REALIGNING THE SACROILIAC JOINT

CROSS REFERENCE TO RELATED APPLICATIONS

This is a divisional patent application that claims benefit from U.S. national stage application Ser. No. 17/290,094 filed on Apr. 29, 2021, which claims priority from PCT patent application serial no. PCT/US2019/059270 filed on Oct. 31, 2019, which claims benefit from U.S. provisional patent application Ser. No. 62/753,575 filed on Oct. 31, 2018, which are herein incorporated by reference in their entirety.

FIELD

The present disclosure generally relates to systems and methods for fixating, fusing, and/or realigning joints in the body and particularly to a system and method for the realignment, fixation, or fusion of the sacroiliac joint.

BACKGROUND

Misalignment or mechanical instability of the sacroiliac (SI) joint can result from many causes such as degenerative disease, spinal deformity, or trauma and can result in pain and immobility. SI joint instability may be treated by fusion, fixation, or otherwise re-alignment of the sacrum with the ilium. Existing strategies for SI joint fusion involve the installation of rods or screws to fix the sacrum and the ilium together, however, these methods can come with significant limitations such as pull-out, failure or misalignment upon installation, which can result in permanent misalignment of the joint.

It is with these observations in mind, among others, that various aspects of the present disclosure were conceived and developed.

BRIEF DESCRIPTION OF THE DRAWINGS

FIG. 17A is an exploded view of a ring of the coupler of FIG. 15 having a channel defined through the ring for insertion of a screw;

Corresponding reference characters indicate corresponding elements among the view of the drawings. The headings used in the figures do not limit the scope of the claims.

DETAILED DESCRIPTION

Figure 1:
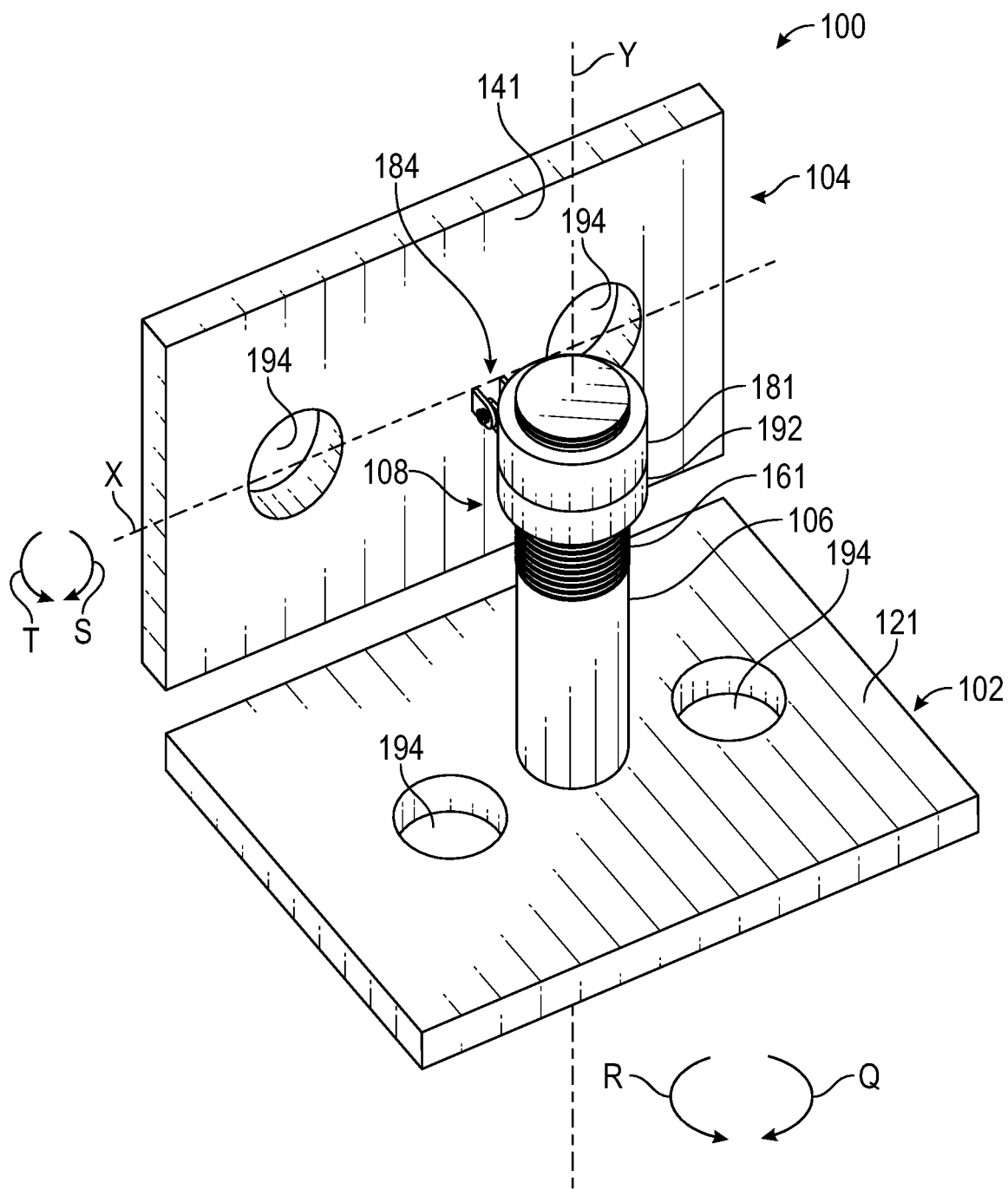
FIG. 1 is a perspective view of a first embodiment of a coupler.
Figure 2:
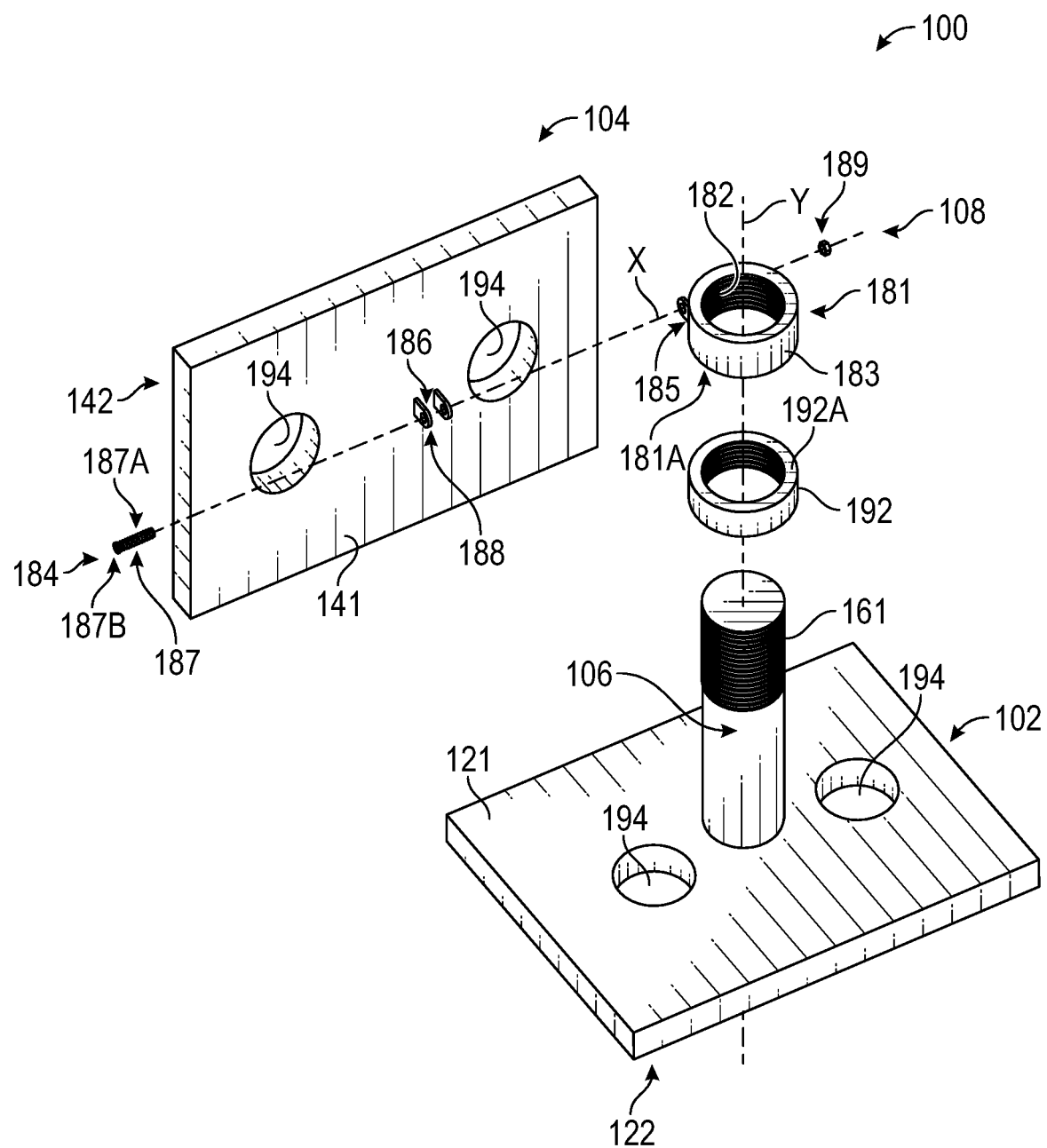
FIG. 2 is an exploded view of the coupler of FIG. 1.
Figure 3:
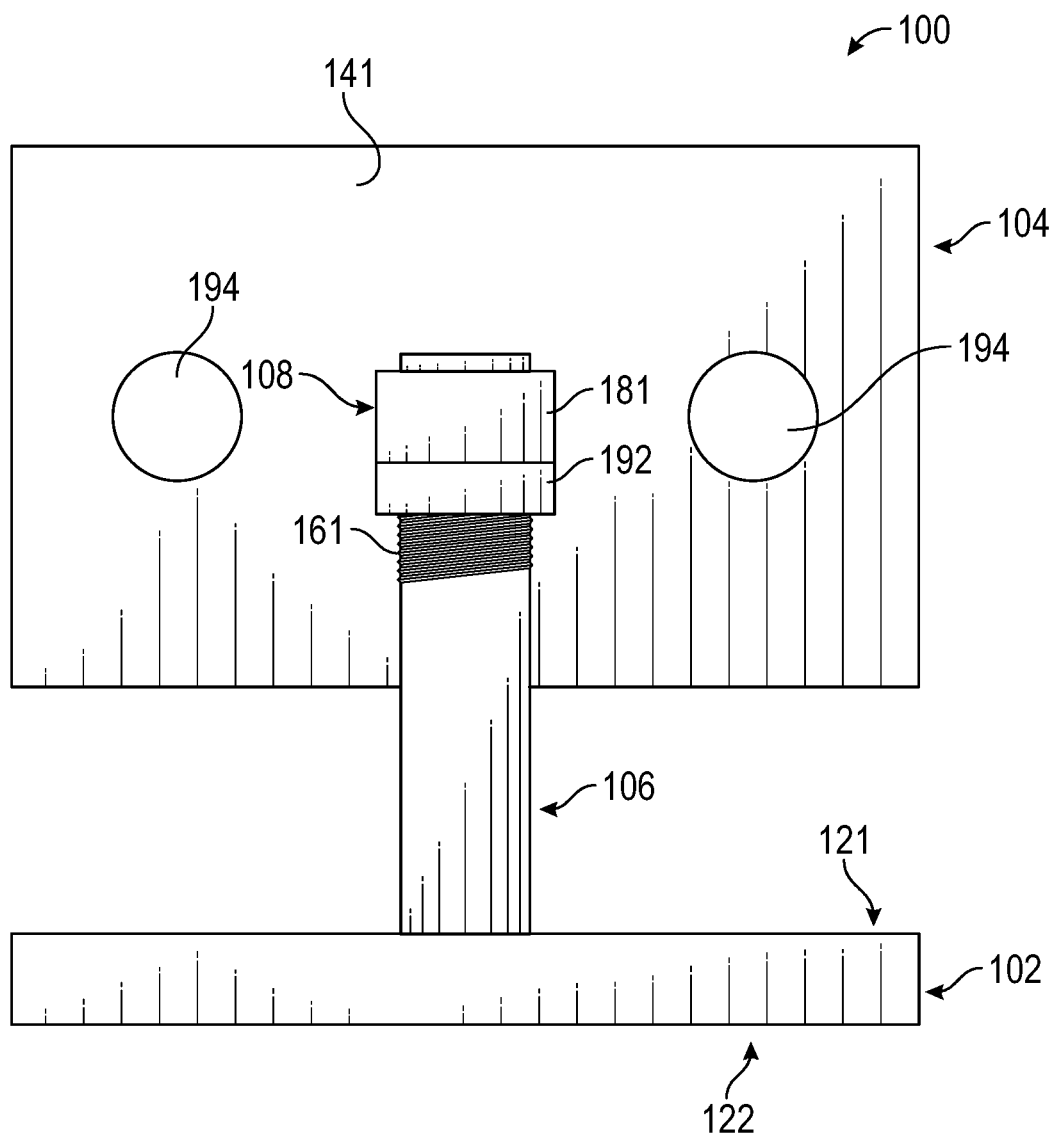
FIG. 3 is a frontal view of the coupler of FIG. 1.

Various embodiments of a sacroiliac joint coupler having a base plate and an angled plate for respective engagement with the sacrum and ilium are described herein. In some embodiments, the sacroiliac joint coupler includes a bolt having a threaded distal end extending from a top face of the base plate and a fastener that couples the distal end of the bolt to the angled plate. In addition, some embodiments of the fastener may include a hinge allowing a user to rotate the angled plate about a lateral axis X relative to the base plate and an inner threading for engagement with the threaded distal end of the bolt, thereby allowing for rotation of the angled plate about a vertical axis Y or alteration of height of the angled plate relative to the base plate. Other embodiments of the fastener include a locking ball joint that allows for changing the orientation of the angled plate about the lateral axis X or the orientation of the angled plate about the vertical axis Y, wherein the locking ball joint includes an inner threading for engagement with the threated distal end of the bolt for altering the height of the angled plate relative to the base plate. In operation, the base plate is screwed into the sacrum and the angled plate is screwed into the ilium and the orientation of the angled plate about the lateral axis X, the orientation of the angled plate about the vertical axis Y, and the height of the angled plate relative to the base plate can be manually adjusted such that the sacrum and ilium are re-aligned and held in place. In some embodiments, the sacroiliac joint coupler may be used in conjunction with a wedge-shaped implant in which the implant may be installed between the sacrum and the ilium and packed with a bone graft material such that the sacrum and ilium are fused together. Referring to the drawings, embodiments of the sacroiliac joint coupler are illustrated and generally indicated as 100, 200 and 300 in FIGS. 1-19 and 24. An embodiment of the implant is illustrated and generally indicated as 400 in FIGS. 20-24.

Figure 9:
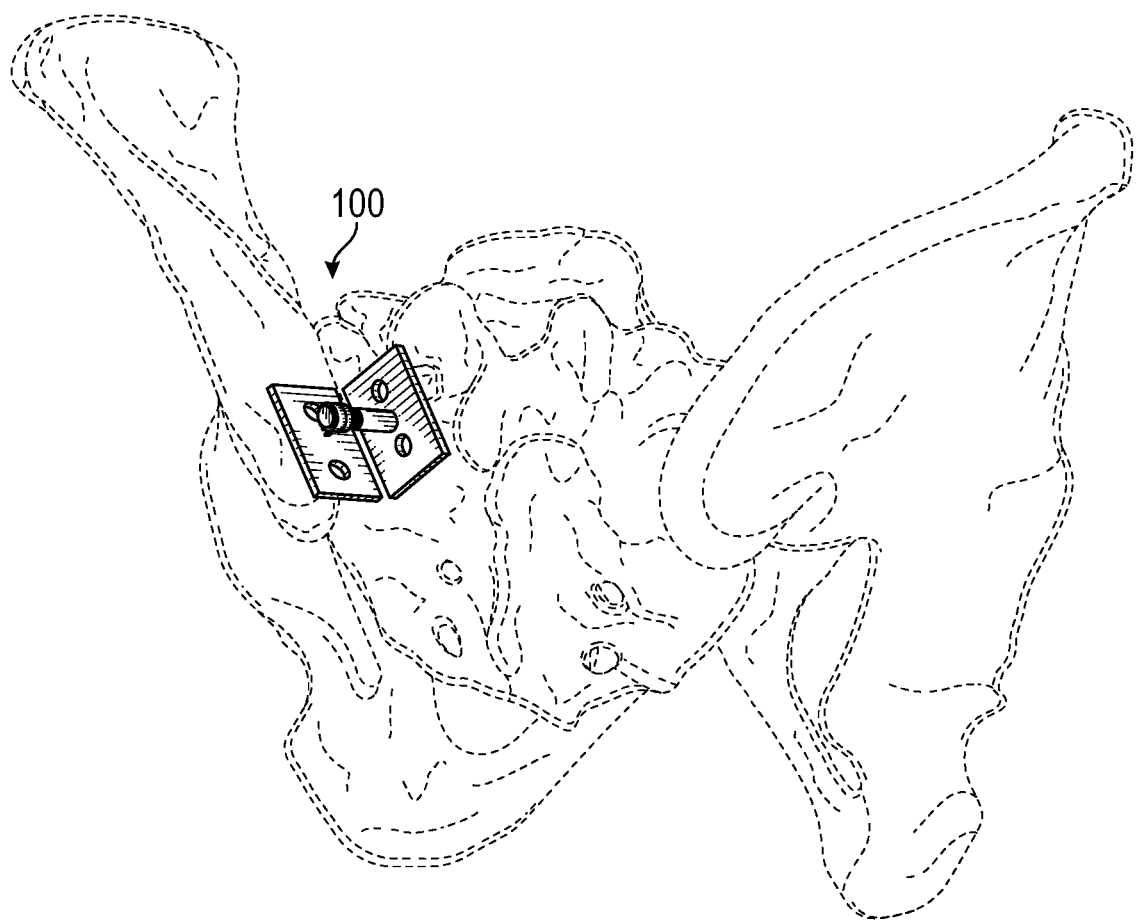
FIG. 9 is an anatomical perspective of the coupler of FIG. 1 installed within a sacroiliac joint.
Figure 10:
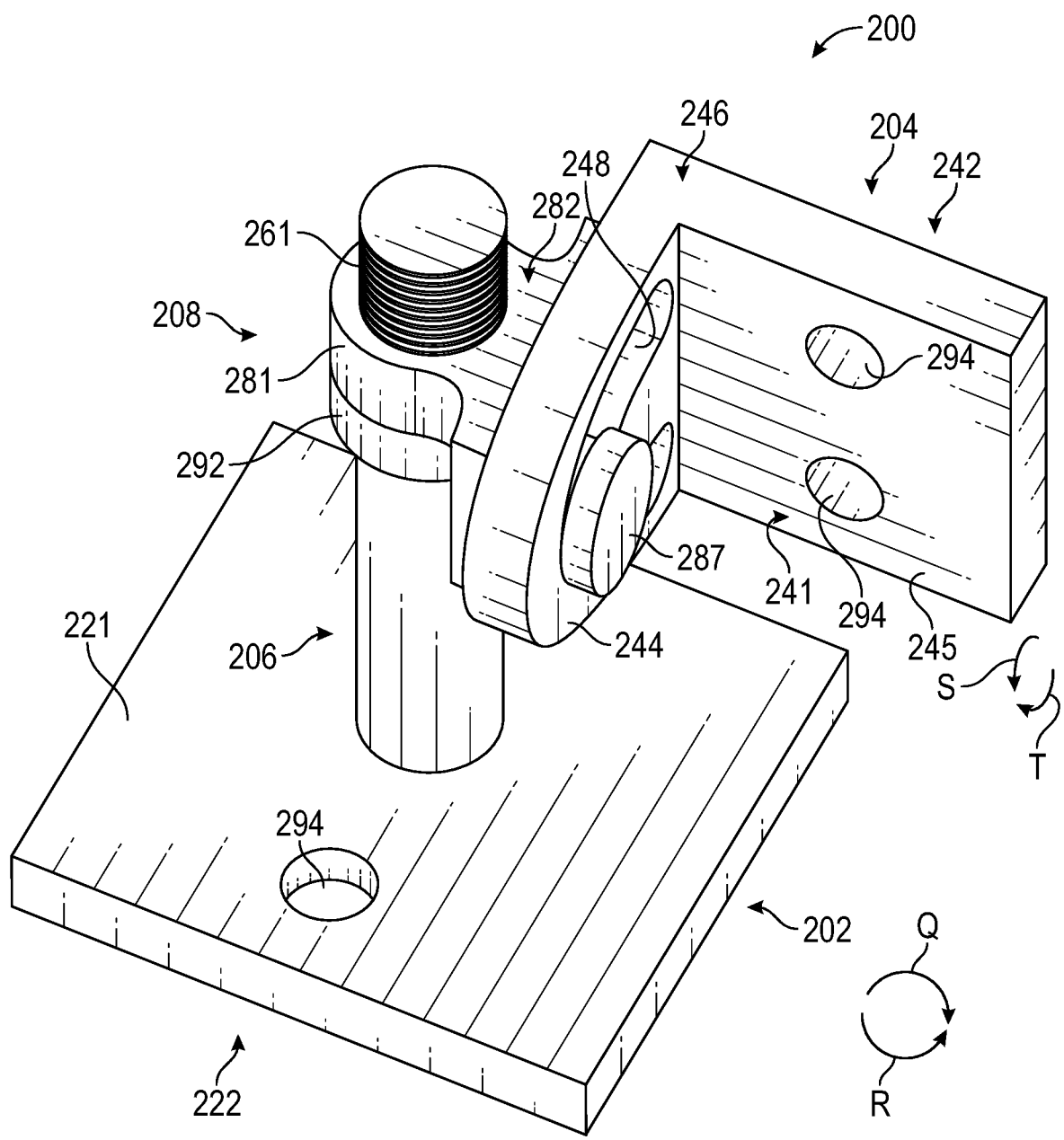
FIG. 10 is a perspective view of a second embodiment of a coupler.

Referring to FIGS. 1-9, a first embodiment of a sacroiliac joint coupler 100 is illustrated. The sacroiliac joint coupler 100 includes a base plate 102 defining a bolt 106 protruding upward from a top face 121 of the base plate 102, wherein the bolt 106 defines a threaded free end 161. In some embodiments, the coupler 100 includes an angled plate 104 operably connected with the base plate 102 by way of a fastener 108, in which the fastener is engaged with the threaded free end 161 of the bolt 106 and a first face 141 of the angled plate 104. In some embodiments, the fastener 108 includes a fastener nut 181 and a hinge 184 which provide a mechanism for rotating the angled plate 104 about a lateral axis X and a vertical axis Y, and for also altering a height of the angled plate 104 relative to the base plate 102. In most embodiments of the coupler 100, the base plate 102 and the angled plate 104 may define a plurality of holes 194 formed through the base plate 102 and the angled plate 104 for installation of one or more screws (not shown). A bottom face 122 of the base plate 102 may be screwed onto or into a sacrum of a patient and a second face 142 of the angled plate 104 may be screwed onto or into an ilium of a patient for mechanical alignment of the sacrum and ilium using the sacroiliac joint coupler 100. In this manner, altering the height and/or orientation of the angled plate 104 about the lateral X axis or the vertical Y axis allows re-alignment of the sacrum with the ilium. The coupler 100 is shown in FIG. 9 installed within the sacroiliac joint.

The fastener 108 comprises the fastener nut 181 defining an inner threading 182 and an exterior surface 183. The inner threading 182 is operably engaged with the threaded free end 161 of the bolt 106. In some embodiments, the exterior surface 183 of the fastener nut 181 defines a first hinge body 185, wherein the first hinge body 185 is configured for operative engagement with a second hinge body 186 defined on the first face 141 of the angled plate 104, which collectively forms the hinge 184. In some embodiments shown in FIG. 2, the hinge 184 of the fastener 108 further includes a plurality of hinge apertures 188, a hinge bolt 187 and a hinge nut 189 oriented around a lateral axis X for adjustment and locking of an orientation about the X axis.

The hinge bolt 187 includes a head 187A located lateral to a first side 184A of the hinge 184 and a threaded axial portion 187B disposed through a hinge channel collectively formed by the plurality of hinge apertures 188. The hinge nut 189 is located lateral to an opposite second side 184B of the hinge 184 and is operably engaged with the threaded axial portion 187B of the hinge bolt 187 such that the hinge 184 is secured between the head 187A of the hinge bolt 187 and the hinge nut 189. In some embodiments, the hinge nut 189 can be permanently affixed to the opposite second side 184B of the hinge 184. In other embodiments, the hinge nut 189 can be detachable from the opposite second side 184B of the hinge 184.

Figure 4:
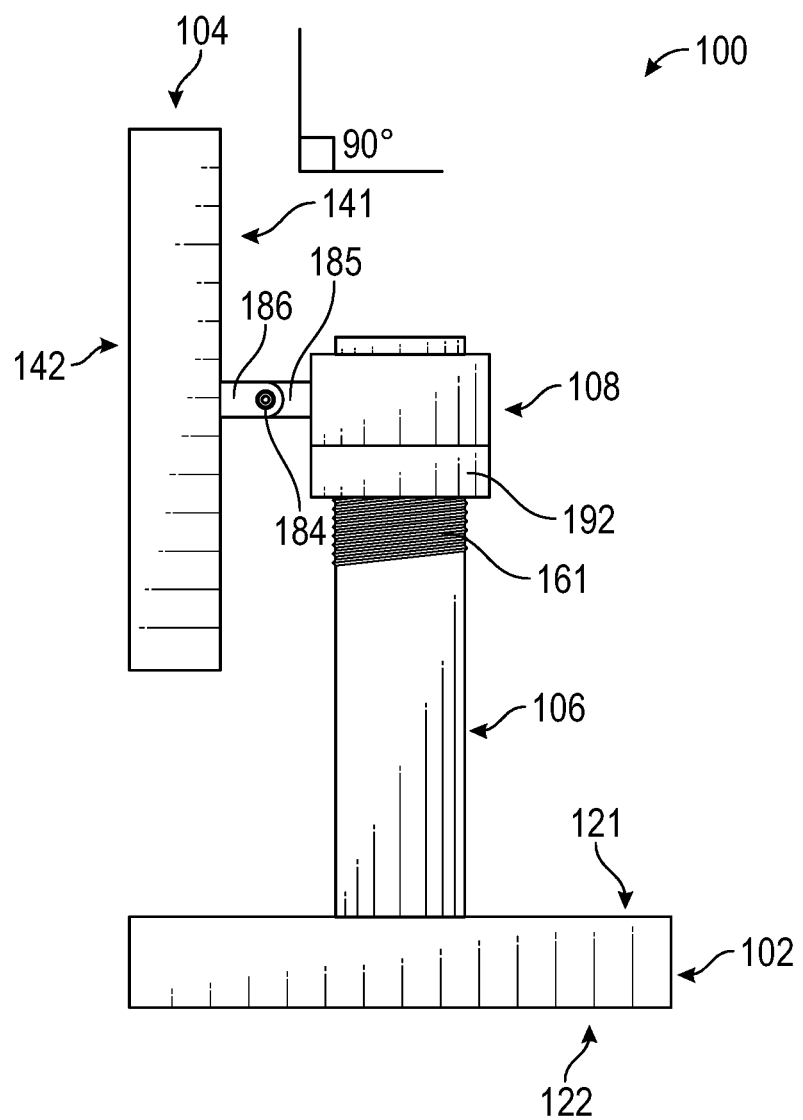
FIG. 4 is a side view of the coupler of FIG. 1 showing a default hinge incidence angle $\varphi=90°$.
Figure 6:
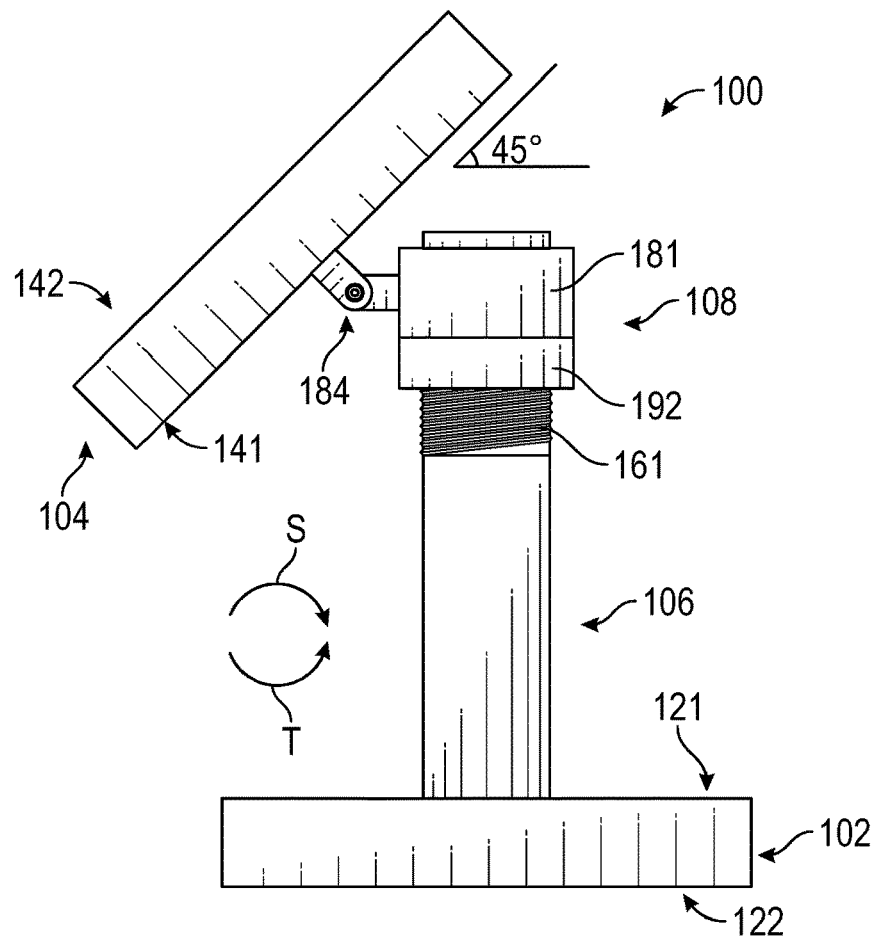
FIG. 6 is a side view of the coupler of FIG. 1 showing a hinge incidence angle $\varphi=45°$.

The angled plate 104 may be rotated around the lateral axis X defined by the hinge 184 until the desired orientation of the angled plate 104 about the X axis is achieved. One orientation of the angled plate 104 about the lateral axis X is shown in FIG. 4 at 90 degrees and in FIG. 6 at 45 degrees. To orient the angled plate 104 about the X axis, the hinge 184 is loosened by rotating the hinge bolt 187 or the hinge nut 189 in a clockwise or counterclockwise direction T (as shown in FIG. 6) and the orientation of the angled plate about the X axis is manually altered. Once the desired orientation about the X axis is achieved, the hinge 184 may be manually locked by rotating the hinge bolt 187 or the hinge nut 189 in an opposite clockwise or counterclockwise direction S until the hinge 184 is fixed between the head 187A (FIG. 6) of the hinge bolt 187 and the hinge nut 189 such that the orientation of the angled plate 104 about the X axis cannot be altered without manual intervention.

Figure 5:
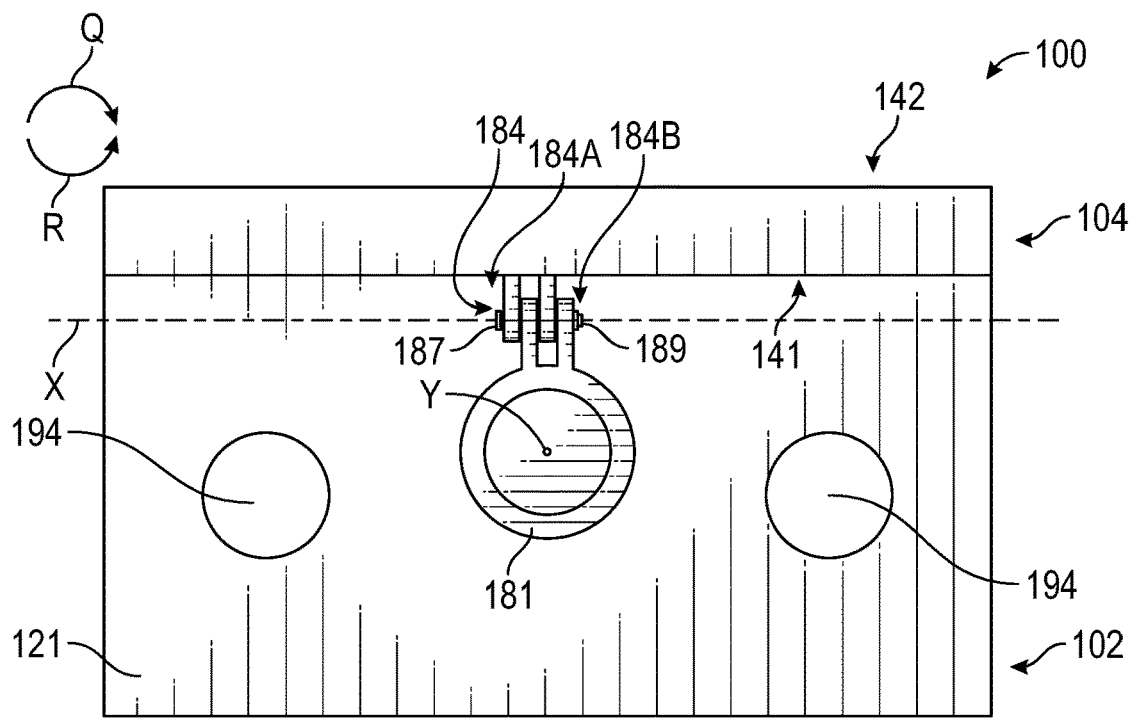
FIG. 5 is a top view of the coupler of FIG. 1 showing a default rotational angle of incidence $\theta=0°$.
Figure 7:
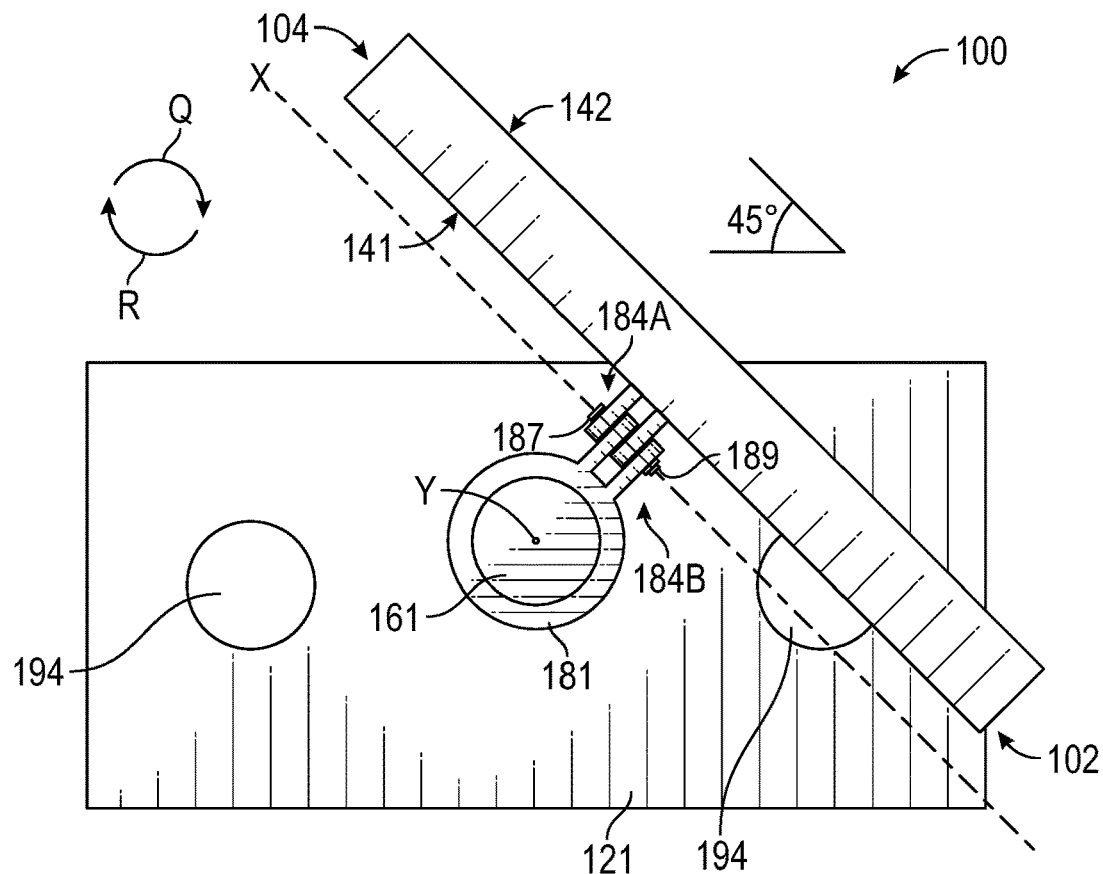
FIG. 7 is a top view of the coupler of FIG. 1 showing a rotational angle of incidence $\theta=45°$.
Figure 8:
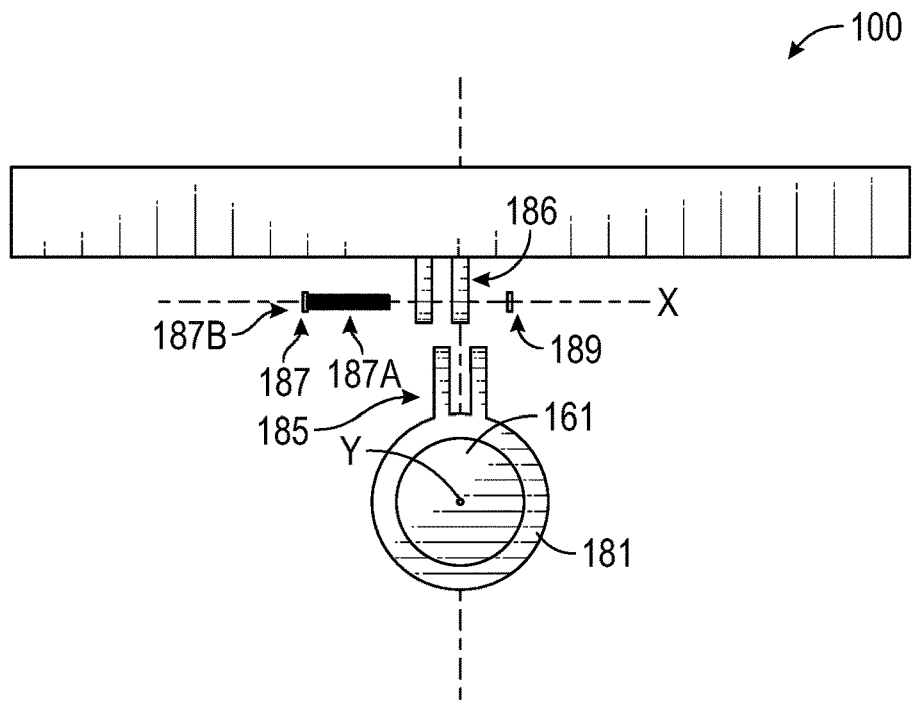
FIG. 8 is an exploded view of an embodiment of a hinge of the coupler of FIG. 1.

As further shown in FIGS. 5 and 7, the fastener nut 181 is operable for manual rotation around a vertical axis Y in a clockwise or counterclockwise direction Q or R for adjustment of an orientation of the angled plate 104 about the Y axis or the height of the angled plate 104 relative to the base plate 102. An orientation of the angled plate 104 about the vertical axis Y is shown in FIG. 5 at 0 degrees and in FIG. 7 at 45 degrees. In some embodiments, a secondary nut 192 defining an upper surface 192A may be engaged with the threaded free end 161 of the bolt 106 such that the upper surface 192A contacts a lower surface 181A of the fastener nut 181. The fastener nut 181 may be rotated around the vertical axis Y until a desired orientation of the angled plate 104 about the Y axis and the desired height are achieved. Once the desired orientation of the angled plate 104 about the Y axis and the desired height are achieved, the fastener nut 181 may be manually locked by rotating the secondary nut 192 in a clockwise or counterclockwise direction R against the fastener nut 181 until the fastener nut 181 and the secondary nut 192 are secured together such that the orientation and height of the angled plate 104 about the Y axis cannot be altered without manual intervention. In some embodiments, a washer (not shown) may be included between the fastener nut 181 and the secondary nut 192 to aid with locking the height and orientation of the angled plate about the Y axis.

Figure 13:
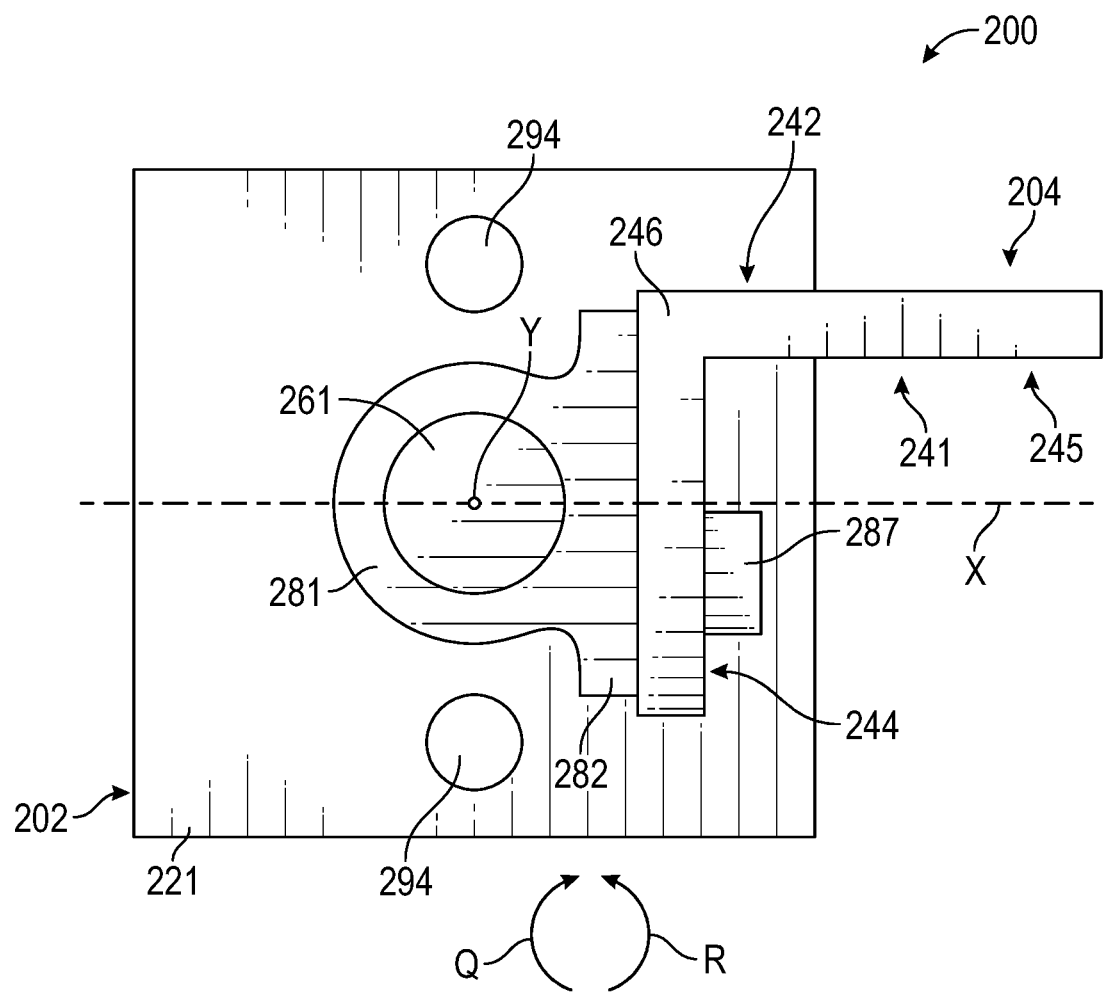
FIG. 13 is a top view of the coupler of FIG. 10.
Figure 14:
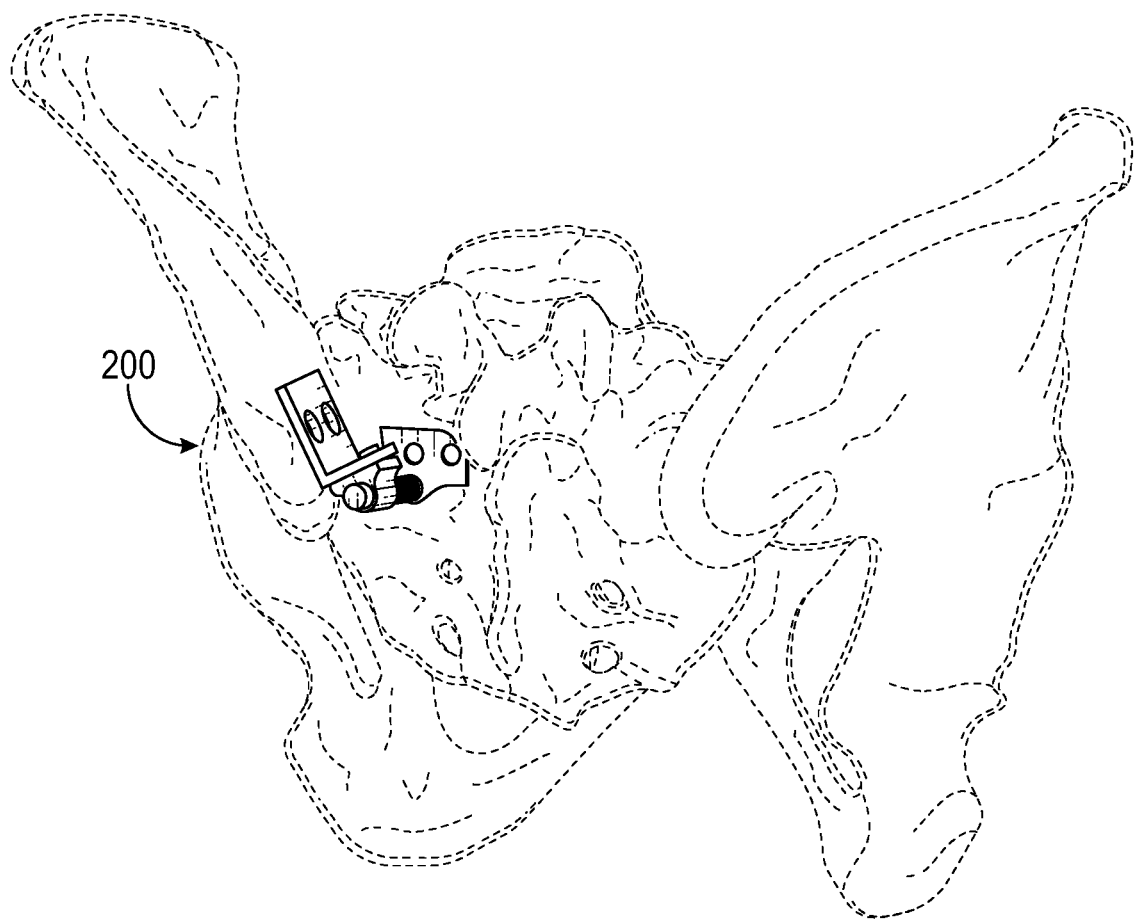
FIG. 14 is an anatomical perspective view of the coupler of FIG. 10 engaged inside the sacroiliac joint without the intradiscal implant.
Figure 15:
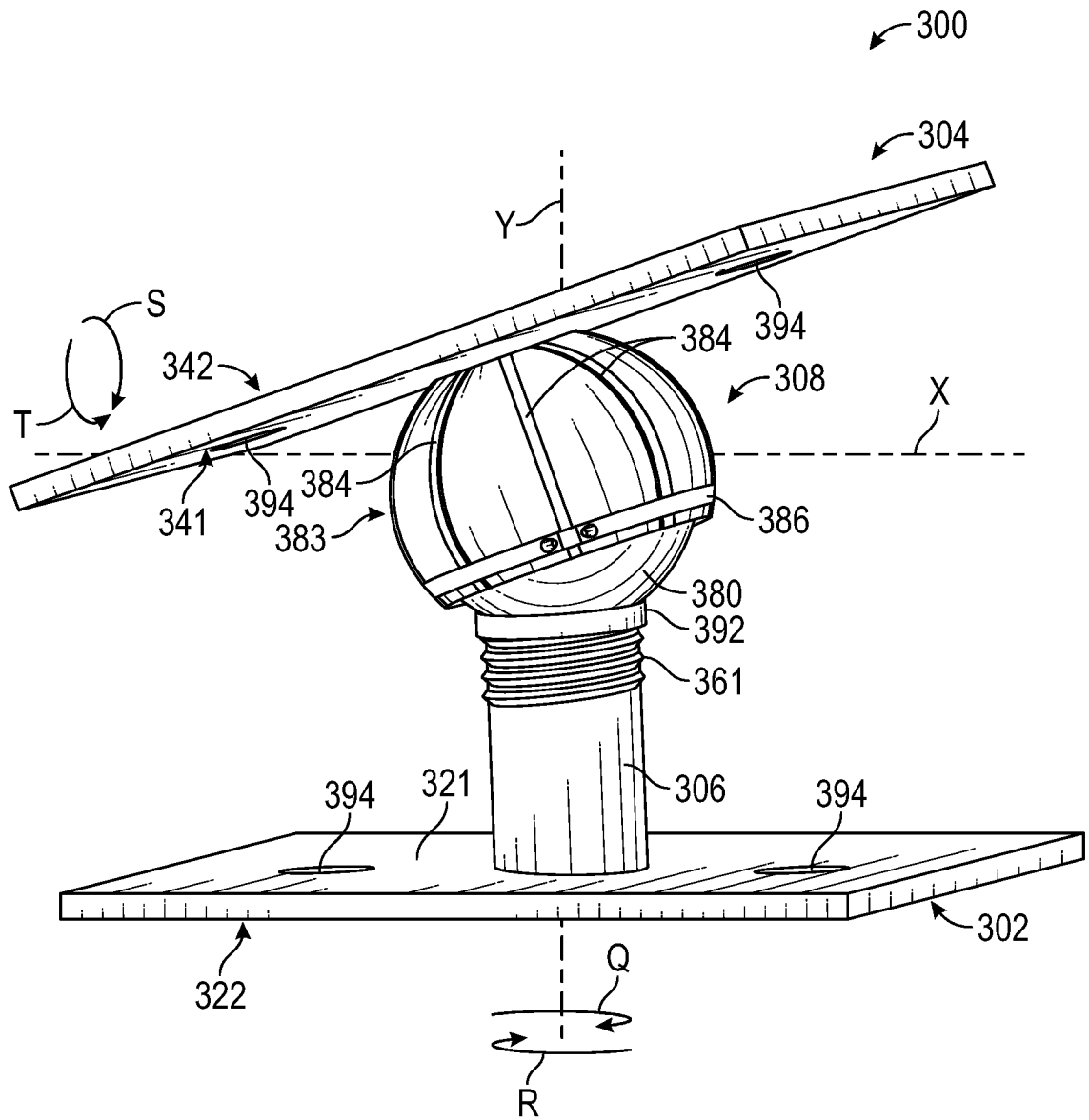
FIG. 15 is a perspective view of a third embodiment of a coupler.
Figure 16:
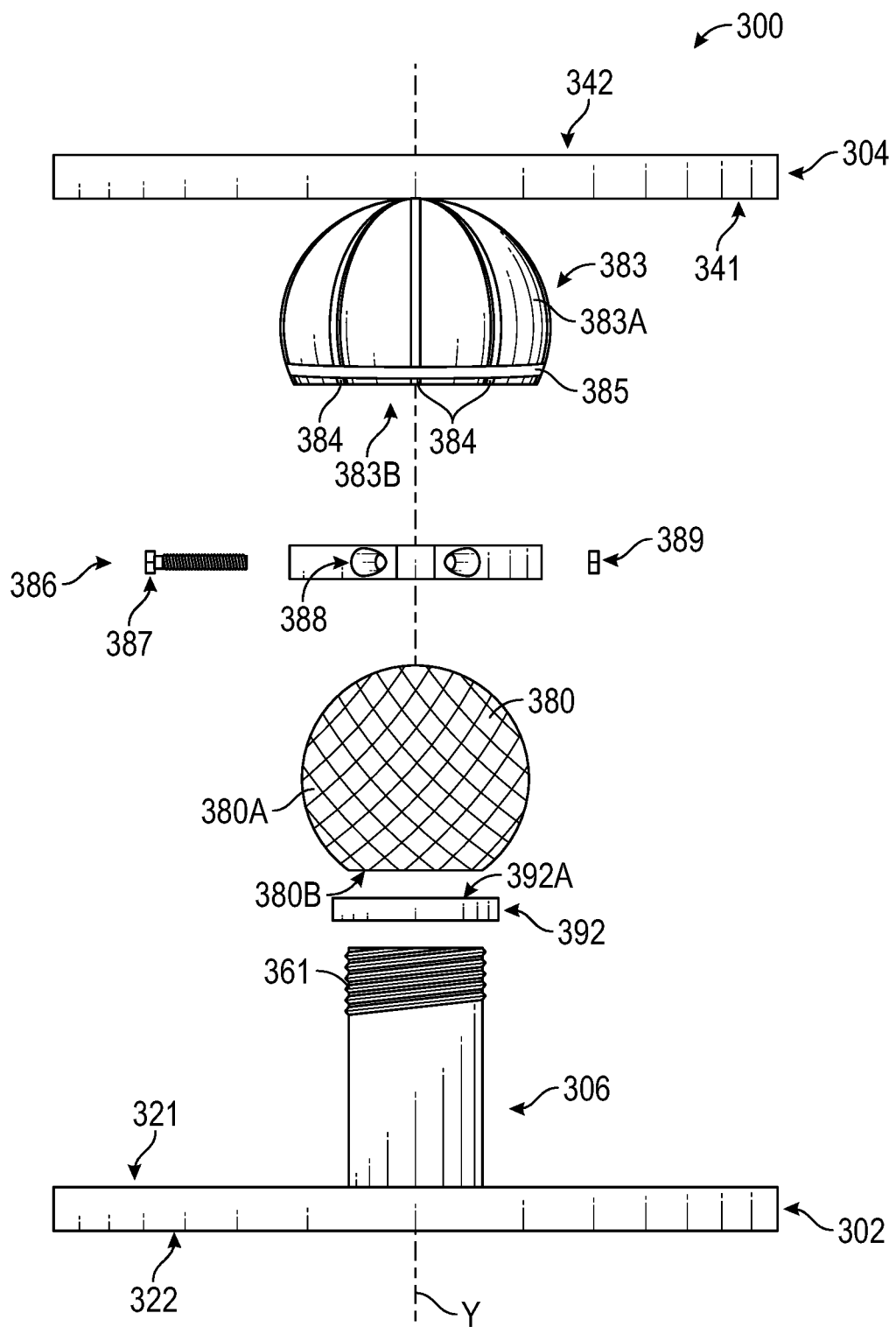
FIG. 16 is an exploded view of the coupler of FIG. 15.

Referring to FIGS. 10-14, a second embodiment of a sacroiliac joint coupler 200 is illustrated. The sacroiliac joint coupler 200 includes a base plate 202 defining a bolt 206 protruding upward from a top face 221 of the base plate 202, wherein the bolt 206 defines a threaded free end 261. In some embodiments, the coupler 200 includes an angled plate 204 operably connected with the base plate 202 by way of a fastener 208, wherein the fastener is engaged with the threaded free end 261 of the bolt 206 and a first face 241 of the angled plate 204. In some embodiments, the fastener 208 may include a fastener nut 281 and a fastener bolt 287 in operative communication with a curved channel 248 defined by the angled plate 204 which provide a means for rotating the angled plate 204 about a lateral axis X and a vertical axis Y, and for altering a height of the angled plate 204 relative to the base plate 202. In some embodiments of the coupler 200, the base plate 202 and the angled plate 204 may define a plurality of holes 294 formed through the base plate 202 and a second portion 245 of the angled plate 204 for installation of one or more screws (not shown), wherein a bottom face 222 of the base plate 202 may be screwed onto a sacrum of a patient and a second face 242 of the angled plate 204 may be screwed onto an ilium of a patient for mechanical alignment of the sacrum and ilium using the sacroiliac joint coupler 200. In this manner, altering the height or orientation of the angled plate 204 about the lateral X axis or the vertical Y axis allows re-alignment of the sacrum with the ilium. The coupler 200 is shown in FIG. 14 installed within the sacroiliac joint.

In some embodiments of the coupler 200 shown in FIGS. 10-14, the angled plate 204 comprises a first portion 244 and the second portion 245. A junction 246 of the first portion 244 and the second portion 245 defines a 90 degree bend angle, shown in FIG. 13. In some embodiments, the first portion 244 of the angled plate 204 further comprises the curved channel 248 defining a curved path 249 configured to receive the fastener bolt 287 of the fastener 208. The fastener bolt 287 further defines a threaded axial portion (not shown) terminating in a head. The width of the curved path 249 is greater than a diameter of the threaded axial portion and is less than the diameter of the head of the fastener bolt 287.

Figure 11:
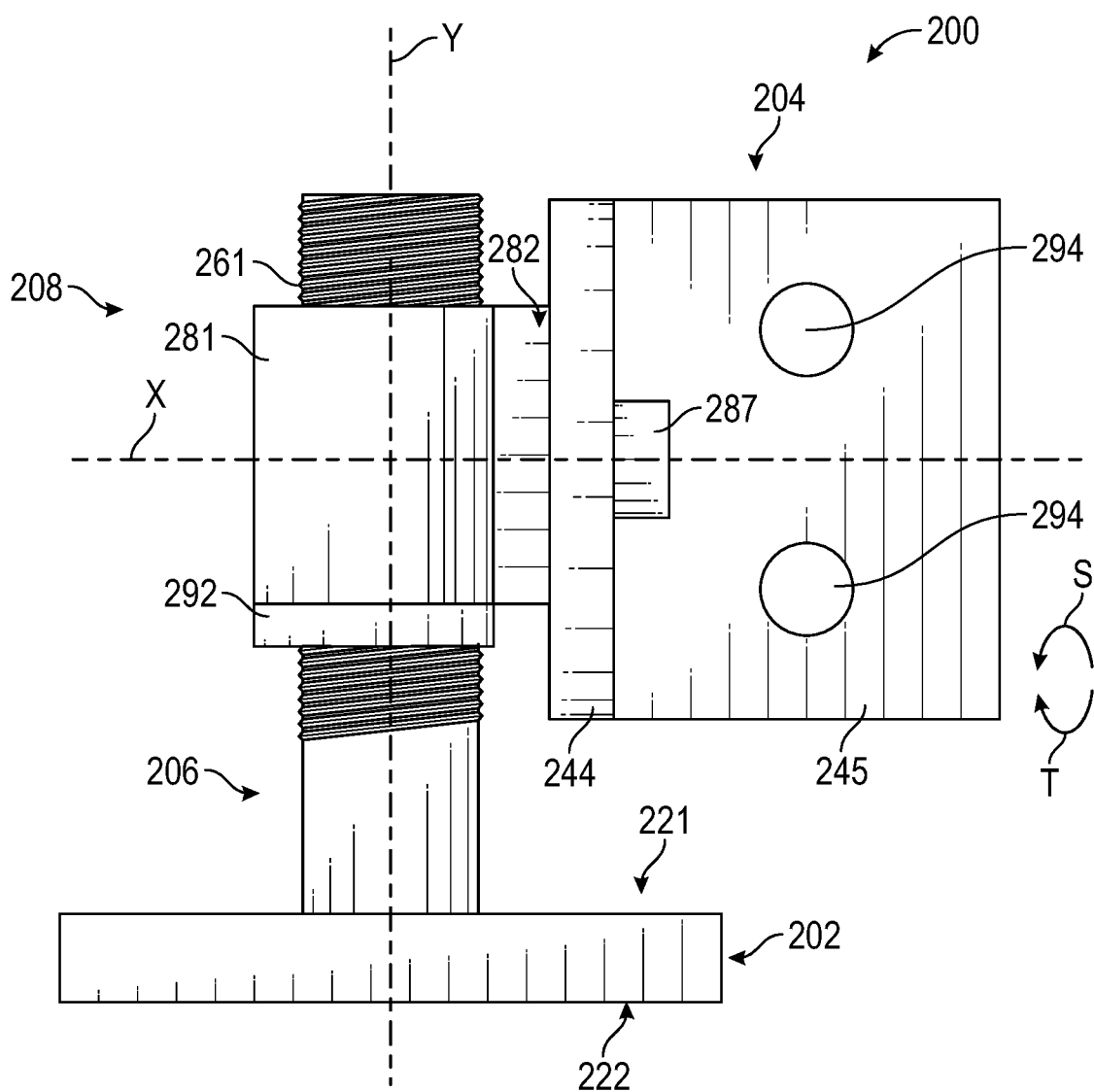
FIG. 11 is a frontal view of the coupler of FIG. 10.
Figure 12:
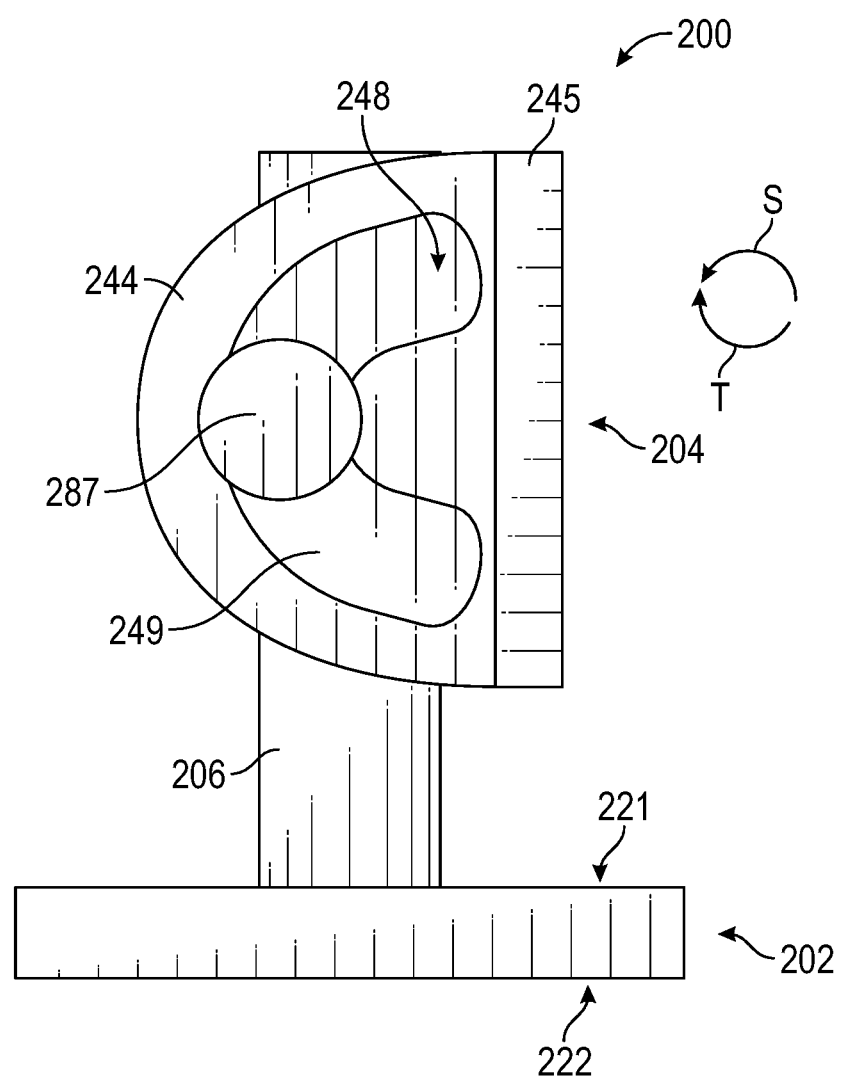
FIG. 12 is a side view of the coupler of FIG. 10.

The fastener 208 includes the fastener nut 281 defining an inner threading (not shown) and an exterior surface. The inner threading is operably engaged with the threaded free end 261 of the bolt 206. In some embodiments, the exterior surface of the fastener nut 281 defines a face 282 formed lateral to the fastener nut 208, as shown in FIG. 11. In some embodiments, the face 282 defines a threaded screw hole (not shown) for engagement with the fastener bolt 287 within the curved channel 248.

In assembly, the first portion 244 of the angled plate 204 is engaged with the face 282 of the fastener 208 and the fastener bolt 287 is inserted through the curved channel 248 of the angled plate 204 and into the threaded screw hole of the fastener 281. The engagement of the fastener bolt 287 with the curved channel 248 and the threaded screw hole clamps the angled plate 204 between the face 282 of the fastener 208.

The angled plate 204 may be rotated around a lateral axis X defined through the first portion 244 of the angled plate 204 until the desired orientation of the angled plate 204 about the X axis is achieved. To alter the orientation of the angled plate 204 about the X axis, the fastener 208 is loosened by rotating the fastener bolt 287 in a clockwise or counterclockwise direction T and the desired orientation of the angled plate 204 about the X axis is then manually altered by rotating the angled plate 204 around the lateral axis X. While the orientation of the angled plate 204 about the X axis is being manually altered, the curved channel 248 is rotated relative to the fastener bolt 287, while the fastener bolt 287 remains loosely engaged within the threaded screw hole. To lock the orientation of the angled plate 204 about the X axis, the fastener 208 is tightened by rotating the fastener bolt 287 in an opposite clockwise or counterclockwise direction S such that the first portion 244 of the angled plate 204 is clamped between the face 282 of the fastener 208 and the head of the fastener bolt 287 as the fastener bolt 287 is screwed into the threaded screw hole such that the orientation of the angled plate 204 about the X axis cannot be altered without manual intervention.

As further shown in FIGS. 11 and 13, the fastener nut 281 is operable for manual rotation around a vertical axis Y in a clockwise or counterclockwise direction Q or R (FIG. 13) for rotation of the angled plate 204 about the vertical axis Y or the height of the angled plate 204 relative to the base plate 202. In some embodiments, a secondary nut 292 defining an upper surface may be engaged with the threaded free end 261 of the bolt 206 such that the upper surface contacts a lower surface of the fastener nut 281. The fastener nut 281 may be rotated around the vertical axis Y until a desired orientation of the angled plate 204 about the Y axis and a desired height are achieved. Once the desired orientation of the angled plate 204 about the Y axis and the desired height are achieved, the fastener nut 281 may be manually locked by rotating the secondary nut 292 in a clockwise or counterclockwise direction R against the fastener nut 281 until the fastener nut 281 and the secondary nut 292 are secured together such that the orientation of the angled plate 204 about the Y axis nor the height can be altered without manual intervention. In some embodiments, a washer (not shown) may be included between the fastener nut 281 and the secondary nut 292 to aid with locking the orientation of the angled plate 204 about the Y axis and the height in position.

Referring to FIGS. 15-18, a third embodiment of a sacroiliac joint coupler 300 is illustrated. The sacroiliac joint coupler 300 includes a base plate 302 defining a bolt 306 protruding upward from a top face 321 of the base plate 302, where the bolt 306 defines a threaded free end 361. In some embodiments, the coupler 300 includes an angled plate 304 operably connected with the base plate 302 by way of a fastener 308, where the fastener is engaged with the threaded free end 361 of the bolt 306 and a first face 341 of the angled plate 304. In some embodiments, the fastener 308 may be as a ball joint, which provides a means for rotating the angled plate 304 about a lateral axis X and a vertical axis Y, and for also altering a height of the angled plate 304 relative to the base plate 302. In most embodiments of the coupler 300, the base plate 302 and the angled plate 304 may define a plurality of holes 394 formed through the base plate 302 and the angled plate 304 for installation of one or more screws, where a bottom face 322 of the base plate 302 may be screwed onto a sacrum of a patient and a second face 342 of the angled plate 304 may be screwed onto an ilium of a patient for mechanical alignment of the sacrum and ilium using the sacroiliac joint coupler 300. In this manner, altering the height and/or orientation of the angled plate 304 about the lateral X axis or the vertical Y axis allows re-alignment of the sacrum with the ilium.

The fastener 308 may be embodied as a ball joint having an inner ball 380 disposed within an outer ball 383, wherein the outer ball 383 defines an outer surface 383A and a textured inner surface 383B forming a half-spherical shape. The inner ball 380 defines a threaded aperture (not shown) defined on a bottom surface of the inner ball 380 for engagement with the threaded free end 361 of the bolt 306. The inner ball 380 further defines a textured exterior surface 380A for engagement with the textured inner surface 383B of the outer ball 383. The outer surface 383A of the outer ball 383 is directly affixed to the first face 341 of the angled plate 304.

Figure 17B:
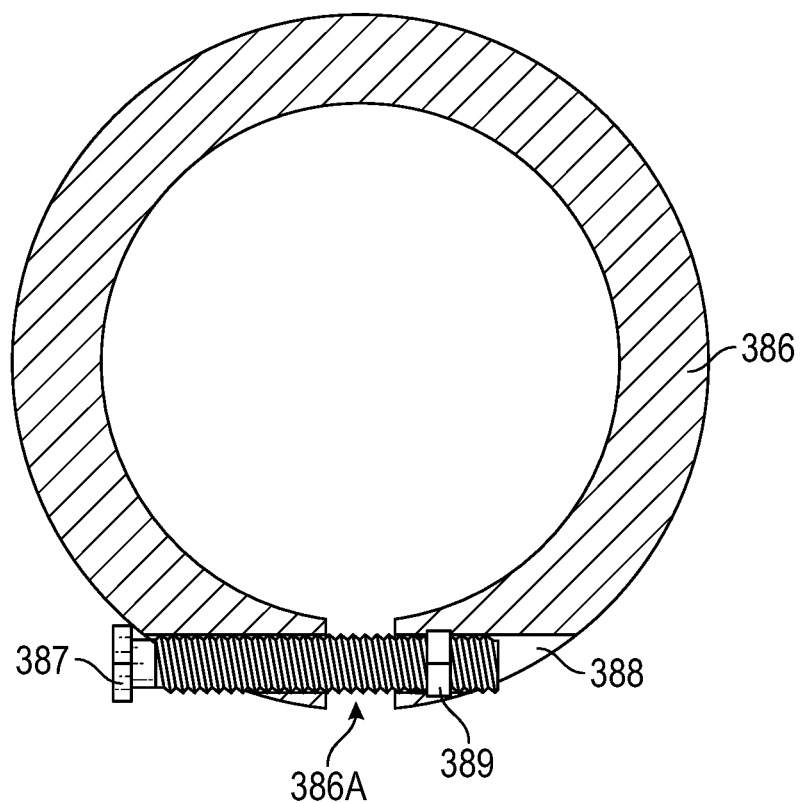
FIG. 17B is a frontal view of the ring of the coupler of FIG. 15 when assembled.
Figure 18:
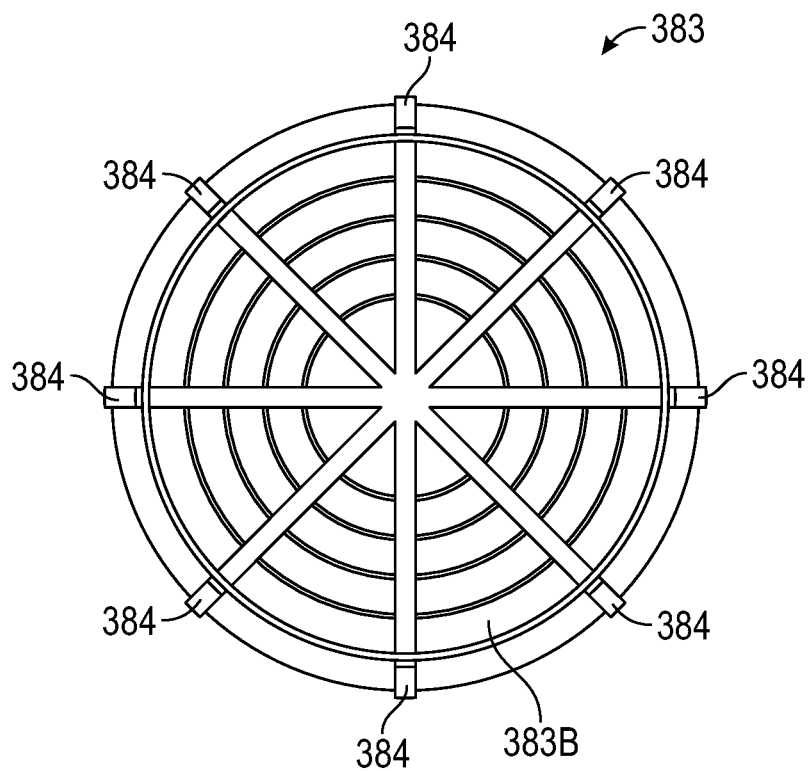
FIG. 18 is a bottom view of an outer ball of the coupler of FIG. 15 having slices and a textured interior surface.
Figure 19:
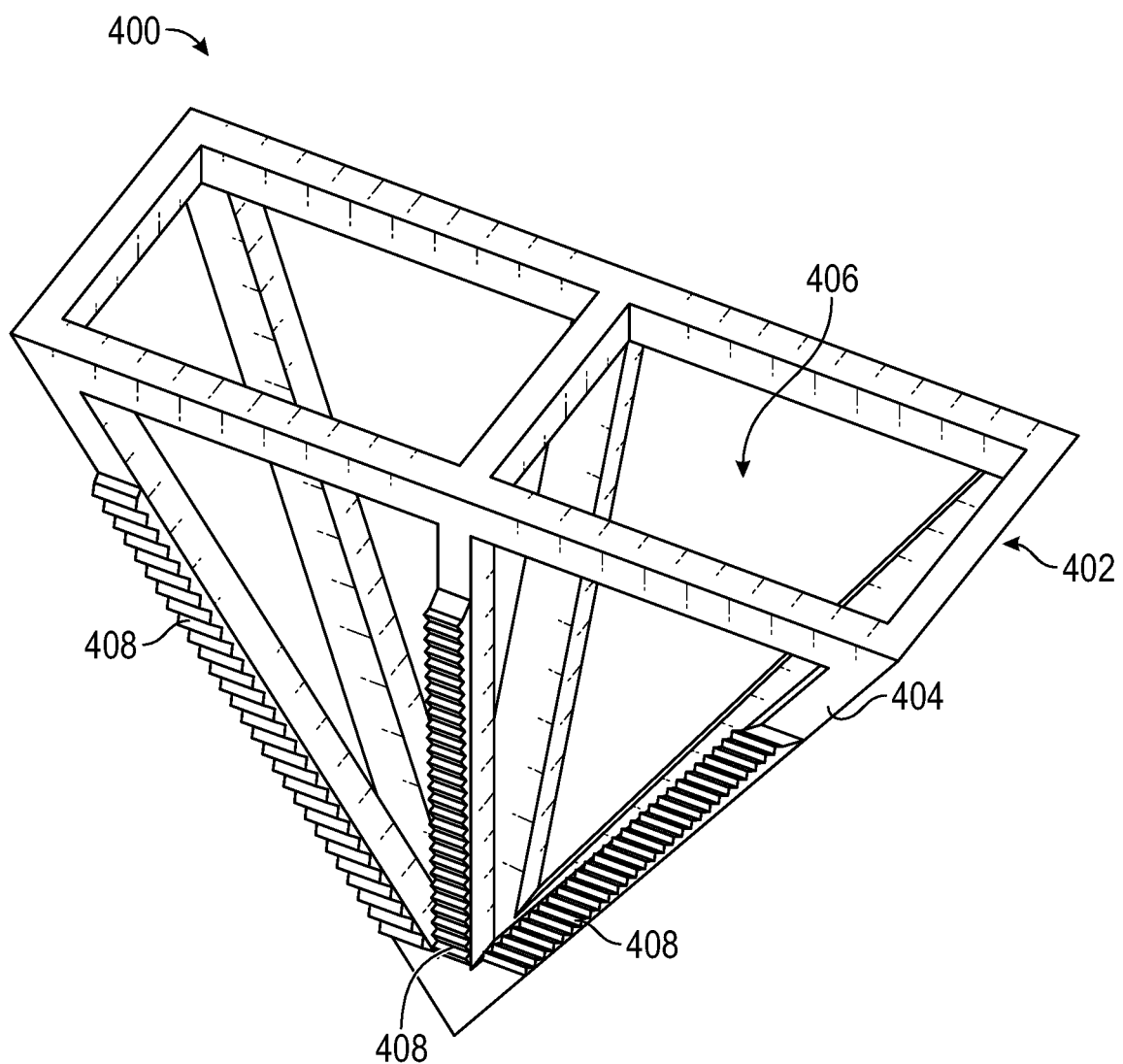
FIG. 19 is a perspective view of an intradiscal implant.

In some embodiments, the outer ball 383 further defines a plurality of slices 384 and a ring recess 385 which allow the outer ball 383 to flex and grip the inner ball 380 when squeezed around the ring recess 385. A ring 386 defining a split 386A is nested around the outer ball 383 within the ring recess 385 such that when the ring 386 is tightened, the outer ball 383 grips the inner ball 380. As shown in FIGS. 17A and 17B, the ring 386 further comprises a channel 388, a screw 387, and a ring nut 389 wherein the screw 387 is inserted into a first end 388A of the channel 388 and mated with the ring nut 389 disposed within a second end 388B of the channel 388 such that when the screw 387 is rotated in a clockwise or counterclockwise direction S (FIG. 15), the ring 386 is tightened and the outer ball 383 grips the inner ball 380. Similarly, rotating the screw 387 in an opposite clockwise or counterclockwise direction T (FIG. 15) will loosen the ring 386 such that the outer ball 383 may be manually disengaged from the inner ball 380.

Altering the orientation of the angled plate 304 about the lateral X axis or the vertical Y axis is achieved by loosening the ring 386 and manually altering the orientation of the angled plate 304 in position relative to the lateral X axis or the vertical Y axis. Locking the orientation of the angled plate 304 relative to the lateral X axis or the vertical Y axis is achieved by rotating the screw 387 in the clockwise or counterclockwise direction S such that the ring 386 is tightened around the outer ball 383 and the outer ball grips the inner ball 380.

As further shown in FIGS. 15-18, the inner ball 380 is operable for manual rotation around a vertical axis Y in a clockwise or counterclockwise direction Q or R for adjustment of the height of the angled plate 304 relative to the base plate 302. In some embodiments, a secondary nut 392 defining an upper surface 392A may be engaged with the threaded free end 361 of the bolt 306 such that the upper surface 392A contacts a lower surface 380B of the inner ball 380. The inner ball 380 may be rotated around the vertical axis Y until a desired height is achieved. Once the desired height is achieved, the inner ball 380 may be manually locked by rotating the secondary nut 392 in a clockwise or counterclockwise direction R against the inner ball 380 until the inner ball 380 and the secondary nut 392 are secured together such that the height cannot be altered without manual intervention. In some embodiments, a washer (not shown) may be included between the inner ball 380 and the secondary nut 392 to aid with locking the height.

Figure 20:
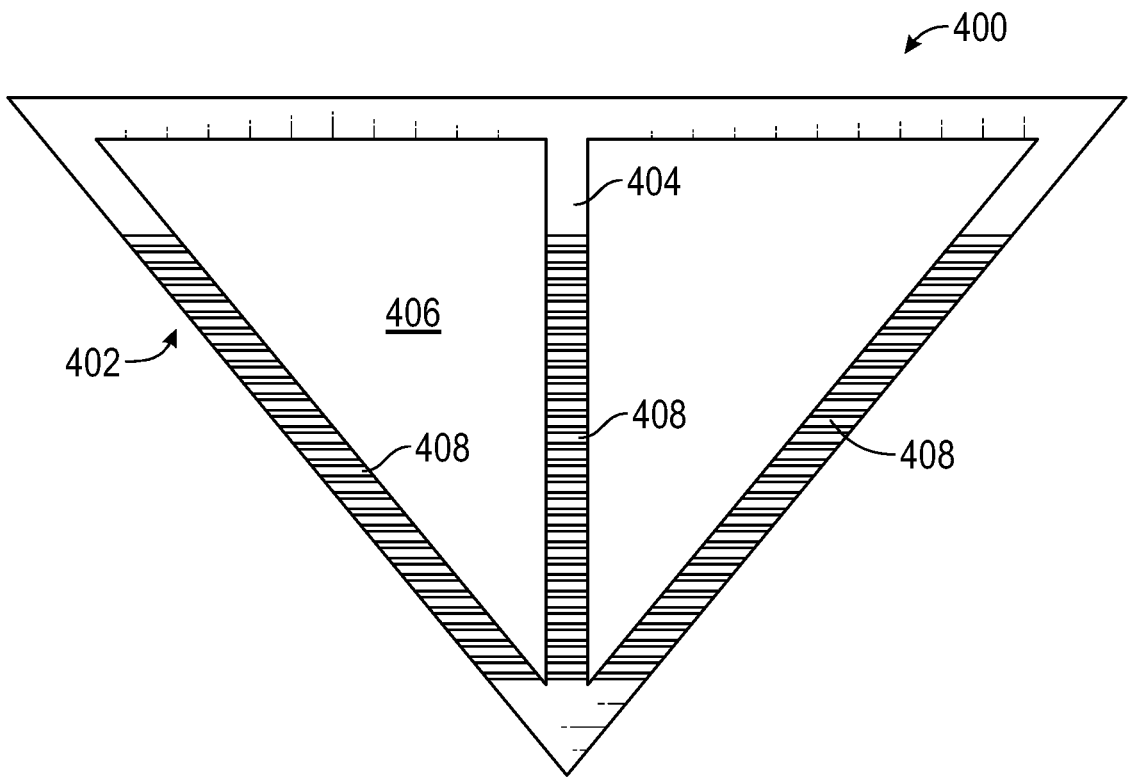
FIG. 20 is a frontal view of the intradiscal implant of FIG. 19.
Figure 21:
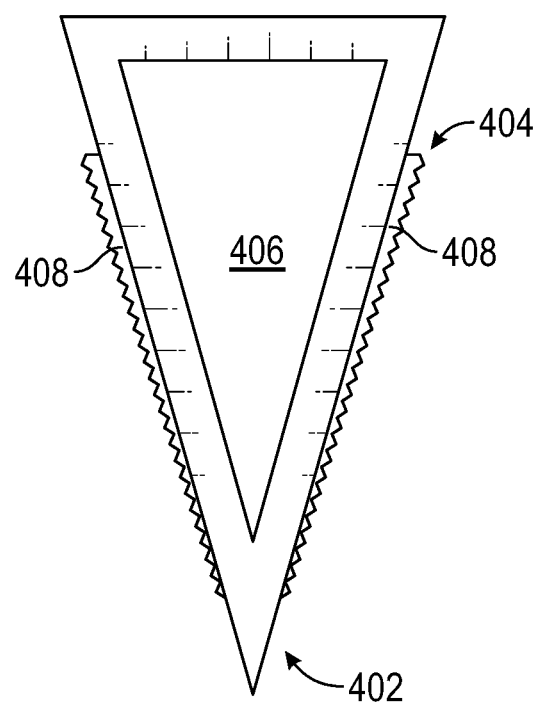
FIG. 21 is a side view of the intradiscal implant of FIG. 19.
Figure 22:
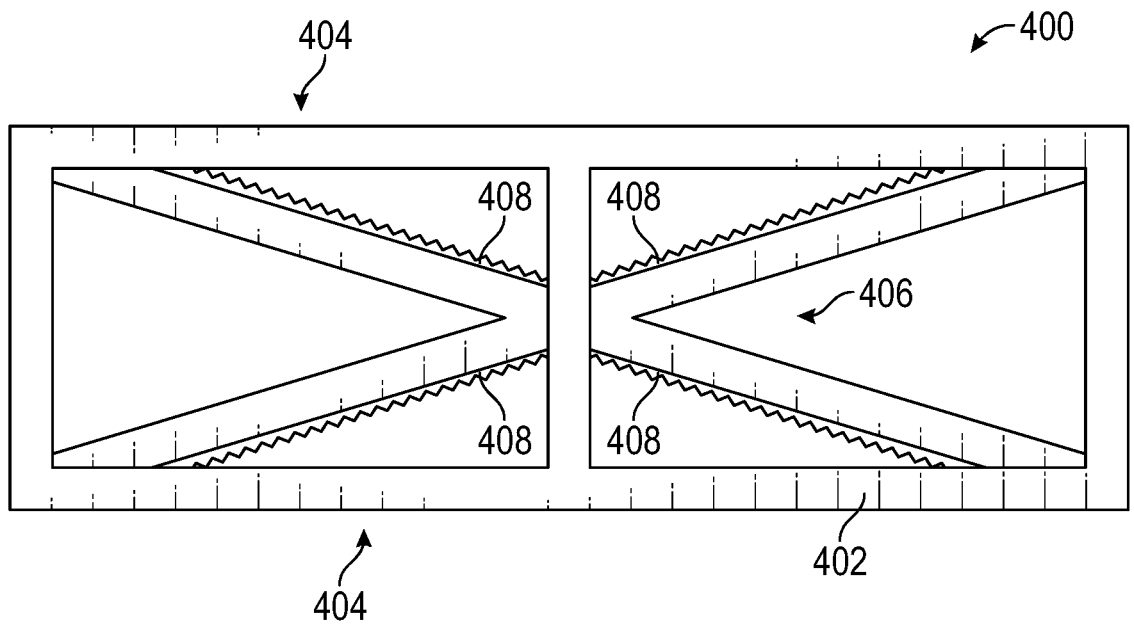
FIG. 22 is a top view of the intradiscal implant of FIG. 19.
Figure 23:
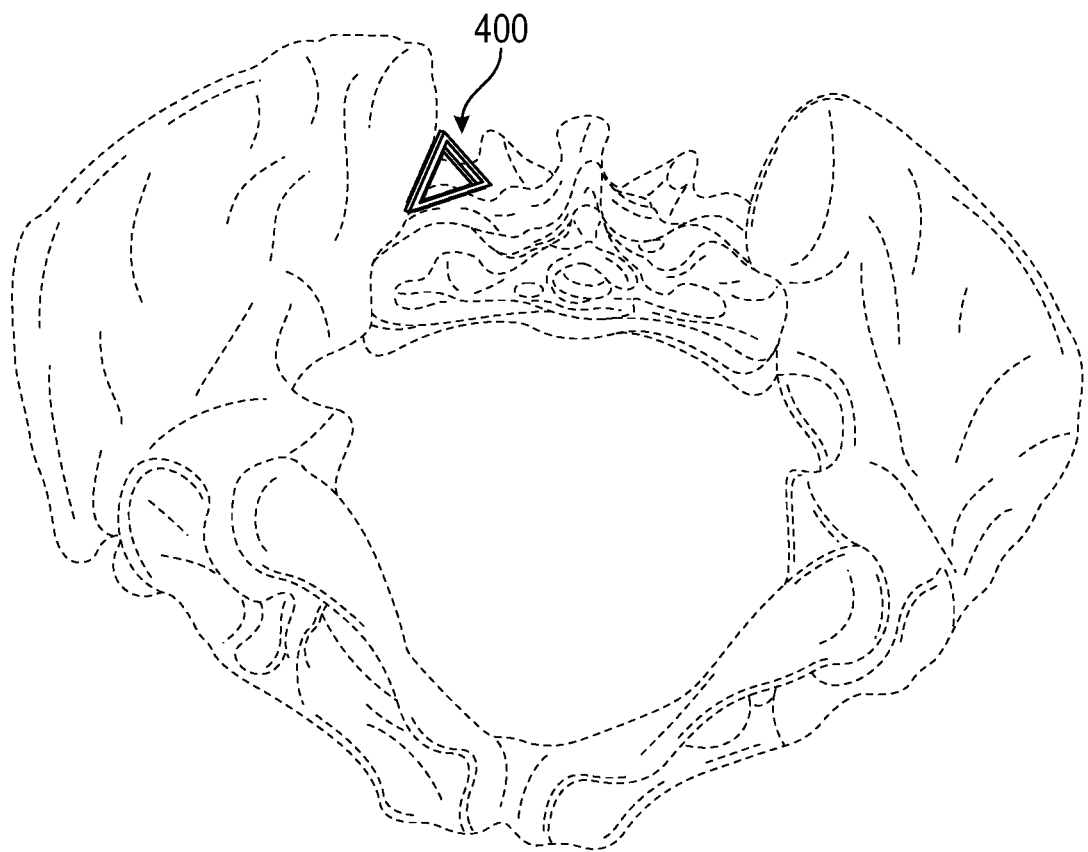
FIG. 23 is an anatomical perspective view of the intradiscal implants of FIG. 19 engaged inside the sacroiliac joint without the coupler.
Figure 24:
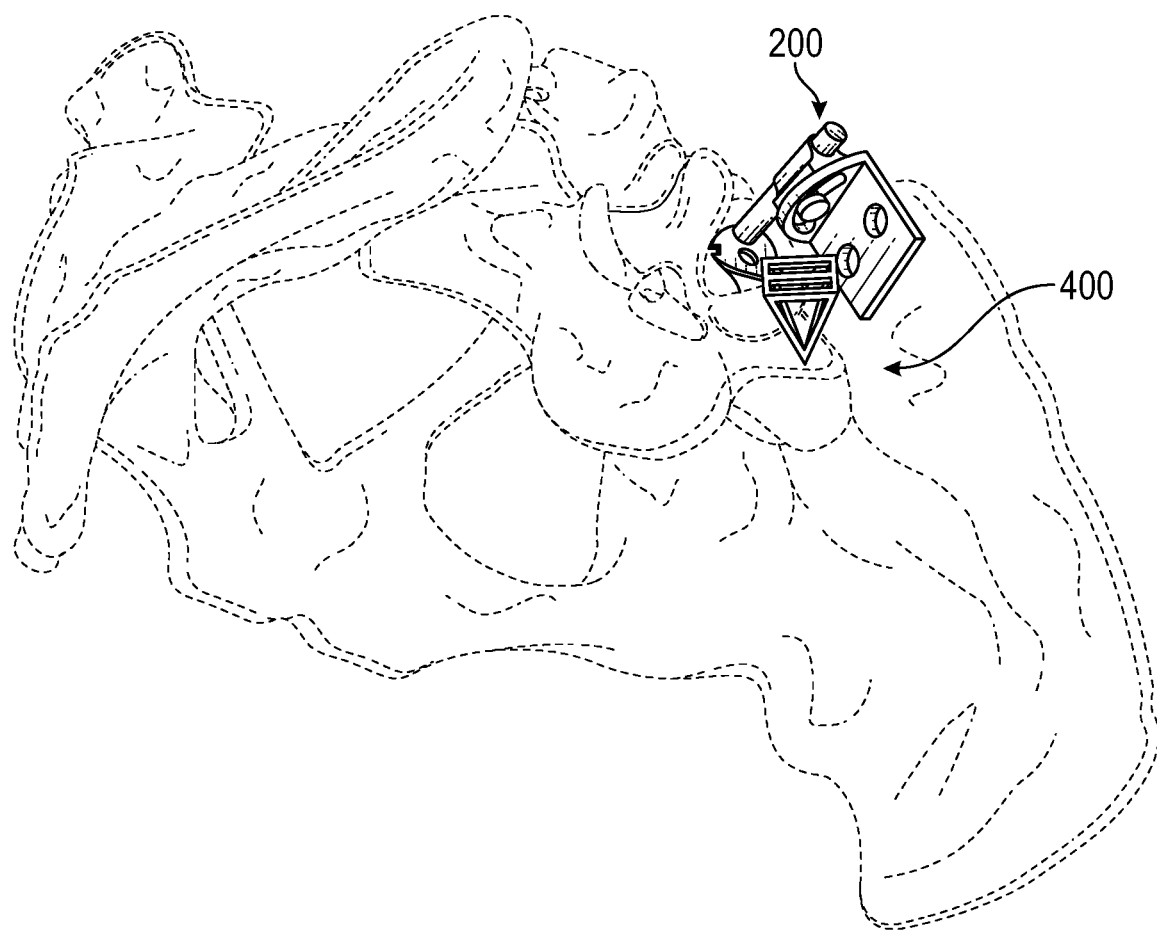
FIG. 24 is an anatomical perspective view of the coupler assembly having the coupler of FIG. 10 and the intradiscal implant of FIG. 19 engaged inside the sacroiliac joint.

An intradiscal implant 400 for insertion within the sacroiliac joint and for use with any one of the embodiments of the coupler 100, 200, or 300 is illustrated in FIGS. 20-24. The intradiscal implant 400 comprises a generally wedge-shaped body 402 defining an exterior surface 404 and a cavity 406. A plurality of teeth 408 may be defined along the exterior surface 404 for engagement with cortical bone surface of both the sacrum and the ilium. During operation, a pointed end of the intradiscal implant 400 is hammered or otherwise inserted between the sacrum and ilium into the sacroiliac joint. As shown in FIGS. 20-22, the wedge-shaped body 402 is of a truss configuration to remain sturdy within the sacroiliac joint. In some embodiments, the cavity 406 is packed with bone graft material to facilitate fusion of the joint. FIG. 23 shows an intradiscal implant 400 inserted into the sacroiliac joint, and FIG. 24 shows the intradiscal implant 400 in use with the coupler 200 inserted into the sacroiliac joint. In this manner, a surgeon may use the intradiscal implant 400 to create extra space for the insertion of the coupler 100, 200, or 300 and then may pack the intradiscal implant 400 with bone graft material after the proper patient-specific orientations and height of the coupler 100, 200, or 300, are induced to ensure proper re-alignment and/or fusion of the sacroiliac joint.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for fusion of the sacroiliac joint, comprising:
   a sacroiliac joint coupler, the sacroiliac joint coupler comprising:
      a base plate defining a top face and a bottom face, wherein the bottom face of the base plate comprises a sacrum-engaging surface;
      a bolt having a threaded free end protruding from the top face of the base plate in a perpendicular relation relative to the base plate; and
      an angled plate defining a first face and a second face, wherein the second face of the angled plate comprises an ilium-engaging surface;
      a fastener engaged with the angled plate,
      wherein the fastener comprises:
         a fastener nut, wherein the fastener nut comprises an inner threading portion engageable with the threaded free end of the bolt;
         a first hinge body defined on an exterior surface of the fastener nut;
         a second hinge body defined on the first face of the angled plate,
         wherein the second hinge body is engaged with the first hinge body; and
         a hinge bolt extending through the first and second hinge bodies;
      wherein the fastener has at least two degrees of freedom; wherein the fastener is engaged with the threaded free end of the bolt such that a first angle about a lateral axis, a second angle about a vertical axis, and a height of the angled plate relative to the base plate may be manually adjusted; and
   a sacroiliac joint implant for use with the sacroiliac joint coupler, the implant defining a wedge-shaped body forming a truss configuration, wherein the implant is configured for insertion between a sacrum and an ilium and wherein the implant comprises a cavity.

2. The system of claim 1, wherein the implant further comprises:
   a plurality of teeth disposed on an exterior surface of the wedge-shaped body, wherein the plurality of teeth is configured for engagement with the sacrum or the ilium.

3. The system of claim 1, wherein the cavity of the implant is configured to receive bone graft material.

4. The system of claim 1, wherein the base plate is sized and configured to be engaged with the sacrum by inserting one or more screws through the base plate and into the sacrum.

5. The system of claim 4, wherein the base plate includes a plurality of holes for engagement with the sacrum.

6. The system of claim 1, wherein the angled plate is sized and configured to be engaged with the ilium by inserting one or more screws through the angled plate and into the ilium.

7. The system of claim 6, wherein the angled plate includes a plurality of holes for engagement with the ilium.

8. The system of claim 1, wherein the hinge bolt comprises:
   a threaded axial portion and a head, wherein the threaded axial portion is inserted through a plurality of hinge apertures defined in the first and second hinge bodies along the lateral axis and wherein a hinge nut is engaged with the hinge bolt such that the first hinge body and the second hinge body are located between the head of the hinge bolt and the hinge nut.

9. The system of claim 8, wherein the orientation of the angled plate about the lateral axis is manually adjusted by rotating the hinge bolt or the hinge nut in a clockwise or counterclockwise direction such that the hinge bolt and the hinge nut are loosened against the first hinge body or the second hinge body and manually adjusting the orientation of the angled plate about the lateral axis and wherein the orientation of the angled plate about the lateral axis is locked in position by rotating the hinge bolt or the hinge nut in an opposite clockwise or counterclockwise direction such that the hinge bolt and hinge nut are tightened against the first hinge body or the second hinge body.

10. The system of claim 8, wherein the fastener further comprises a secondary nut having a superior face engaged below the fastener nut with the threaded free end of the bolt.

11. The system of claim 10, wherein the orientation of the angled plate about the vertical axis and the height of the angled plate relative to the base plate are altered by rotating the fastener nut in a clockwise or counterclockwise direction, and wherein the orientation of the angled plate about the vertical axis and the height of the angled plate relative to the base plate are locked in position by tightening the superior face of the secondary nut against the fastener nut.

* * * * *